(12) United States Patent
Deregnaucourt et al.

(10) Patent No.: US 8,242,110 B2
(45) Date of Patent: Aug. 14, 2012

(54) USE OF ANTIHISTAMINE AGENTS FOR THE PREVENTIVE OR EARLY TREATMENT OF INFLAMMATORY SYNDROMES, IN PARTICULAR THOSE TRIGGERED BY TOGAVIRUSES

(75) Inventors: Jean Deregnaucourt, Paris (FR); Etienne Andre, Seyssinet-Pariset (FR); Jacky Tisne-Versailles, Castres (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 809 days.

(21) Appl. No.: 12/224,830

(22) PCT Filed: Mar. 9, 2007

(86) PCT No.: PCT/EP2007/052237
§ 371 (c)(1), (2), (4) Date: Oct. 8, 2008

(87) PCT Pub. No.: WO2007/101884
PCT Pub. Date: Sep. 13, 2007

(65) Prior Publication Data
US 2009/0069308 A1    Mar. 12, 2009

(30) Foreign Application Priority Data
Mar. 9, 2006    (FR) ..................................... 06 02087

(51) Int. Cl.
*A61K 31/54*    (2006.01)
(52) U.S. Cl. ................................... 514/227.8
(58) Field of Classification Search .............. 514/227.8
See application file for complete search history.

(56) References Cited

U.S. PATENT DOCUMENTS 3,726,976 A * 4/1973 Glasser .......................... 514/186
6,720,318 B2   4/2004 Dib et al.

FOREIGN PATENT DOCUMENTS

| FR | 2 802 101 A1 | 6/2001 |
| JP | 4-89428 A | 3/1992 |
| JP | 2001-151677 A | 6/2001 |
| WO | WO-96/04787 A1 | 2/1996 |

OTHER PUBLICATIONS

Wilson, Annals of Rheumatic Diseases, 1953;12(1):38-39.*
Storms, Journal of Allergy and Clinical Immunology, 2004;114:S146-153.*
Satake et al., Journal of Cardiovascular Pharmacology, 1994;23(4):669-673 (abstract only).*
Toovey et al., Travel Medicine and Infectious Disease, vol. 2, No. 3-4, 2004, pp. 189-191.
Suhrbier et al., Current Opinion in Rheumatology, vol. 16, No. 4, 2004, pp. 374-379.
Stocks et al., Australian Family Physician, vol. 26, No. 6, Jun. 1997, pp. 710-717.
Paganin et al., Presse Medicale 2006, vol. 35, No. 4 II, 2006, pp. 641-646.
Ware et al., Medical Care, vol. 34, No. 3, 1996, pp. 220-233.
Bruce et al., The Journal of Rheumatology, vol. 30, No. 1, 2003, pp. 167-178.

* cited by examiner

*Primary Examiner* — San-Ming Hui
(74) *Attorney, Agent, or Firm* — Birch, Stewart, Kolasch & Birch, LLP

(57) ABSTRACT

The present invention relates to the use of at least one antihistamine agent for the preparation of a medicament for use in the preventive or early treatment of inflammatory syndromes of viral origin, in particular arthritis of the distal joints, more particularly those triggered by togaviruses. The invention also relates to a combination product of at least one antihistamine agent and of at least one antiserotonin agent for its simultaneous, separate or sequential use in preventive or early therapy for inflammatory syndromes of viral origin, in particular arthritis of the distal joints, more particularly those triggered by togaviruses.

12 Claims, No Drawings

USE OF ANTIHISTAMINE AGENTS FOR THE PREVENTIVE OR EARLY TREATMENT OF INFLAMMATORY SYNDROMES, IN PARTICULAR THOSE TRIGGERED BY TOGAVIRUSES

The present invention concerns the novel use of antihistaminic agents to prepare a medicinal product intended for the preventive or early treatment of inflammatory syndromes, more specifically in arthritis of viral origin.

In general, subsequent to localized or diffuse tissue attack, whether by trauma or infection, a complex cascade of reactions is set up by the body to eliminate the infectious agent and to initiate a repair process. This sequence of events is called the inflammatory reaction and associates local phenomena with the production of systemic signals. The triggering of the cascade of inflammatory reactions can have a large number of causes: bacterial, viral, parasitic, mycotic, tumoral, traumatic, physical and/or immunological. The systemic, biological and clinical anomalies ascertained at this time form an inflammatory response syndrome. The production of cytokines by macrophages plays a central role in orchestrating the mechanisms which contribute towards the setting up of an inflammatory reaction. The systemic circulation of the three chief cytokines of inflammation (IL1, IL6 and TNF α) whose production is excessive when the inflammatory response is exacerbated, leads to what is known as the systemic inflammatory response syndrome (SIRS).

The present invention more particularly concerns inflammatory syndromes in which it is chiefly lesions of joint tissue which are observed. Rheumatoid arthritis is an example thereof. Other tissues may marginally be affected e.g. the heart, lungs, skeletal muscles, peripheral vessels or the central nervous system. The aetiology of this disorder, even though largely researched, remains obscure. The triggering factors include infectious agents, heredity, food factors, but also auto-immune reactions. In this latter case, the starting point of response to outside attack is an antigen/antibody reaction leading to an immune complex which is the triggering factor of a sequence of biological phenomena. Alongside this cascade of phenomena intended to combat attack, the immune complexes have pathological potential. Whereas antibodies have two combining sites with antigens for IgG immunoglobulins or five combining sites for IgM immunoglobulins, the antigens are multivalent. The complexes thus formed at the time of this antigen/antibody association have different sizes and solubilities, and their pathological potential depends on their relative proportions. The mechanisms via which the immune complexes can lead to lesions at some tissues have been the subject of numerous studies. In particular, it has been evidenced that they can influence the release of vasoactive agents of platelets, neutrophils and mast cells, both by complement-dependent action and non-complement dependent action. Amongst these agents, vasoactive amines increase vascular permeability, which causes extravasation and the depositing of a large quantity of antigen/antibody complexes at peri- and extra-vascular membranes. An inflammatory process is then triggered if polymorphonuclear leukocytes are recruited and accumulate. Lesions may also occur if the antigen/antibody complexes precipitate. Activation of the resulting complement sequence, after phagocytosis of the complex, leads to the release of cytokines and lysosomial enzymes from polymorphonuclear leukocytes and monocytes. These enzymes can be the cause of an increase in inflammation, giving rise to lesions at different tissues.

Aside from rheumatoid arthritis, a chronic inflammation, there are joint inflammations derived from bacterial, mycosic or viral infections. Acute infectious arthritis is generally of bacterial or viral origin. With regard to bacterial arthritis, the bacteria involved are gonococci, staphylococci, streptococci, pneumococci, Haemophilus, Spirochetes. Non-gonococcal arthritis is usually caused by *Staphylococcus aureus*, Spirochetes, streptococci or other gram-bacteria. With respect to acute viral arthritis, the chief identified causes are B19 parvoviruses, flaviviruses, Hepatitis B and C viruses, the rubella and measles viruses, togaviruses (including alphaviruses). Other pathologies are also associated with arthralgia and arthritis. These are chicken pox, mumps, adenovirus illnesses, Coxsackie A9, B2, B3, B4 and B6 viruses, and Epstein-Barr mononucleosis.

In all these situations, the infection leads to an inflammatory reaction at the joints following a process similar to that described above.

The clinical signs of infectious arthritis are joint pain and tumefaction at the site of inflammation. This may affect several joints. These signs are usually of sudden onset, accompanied by fever and shivering. Infections of viral origin are also accompanied by feelings of generalized faintness.

Treatments currently available have recourse to non-steroid anti-inflammatory drugs (NSAIDs) in particular to relieve pain, swelling and stiffness caused by infectious arthritis, but they do not contribute towards preventing joint lesions and their consequences. In stronger doses NSAIDs also help to relieve inflammation. For infectious arthritis of bacterial origin antibiotics are used, but for arthritis of viral origin generally no medication is prescribed so as to treat the cause of the pathology. In most cases the infection subsides spontaneously.

There is therefore a need for active pharmacological substances, capable of acting at an early stage even preventively, to avoid the harmful consequences on the joints of the inflammatory process set up at the time of bacterial or viral infections.

The Applicant has evidenced that some antihistaminic agents can fulfill this purpose.

Antihistamines are substances which oppose the activity of histamine on its specific receptors, and therefore oppose the various reactions caused by this activity. These inhibitors only act selectively, even specifically, on a sub-type receptor, hence there are several classes of antihistamines: H1 antihistamines, H2 antihistamines, H3 antihistamines.

H2 antihistamines are powerful inhibitors of gastric secretion, and are used for ulcer conditions and secondarily against gastro-oesophageal reflux and pyrosis.

H1 antihistamines act against the vascular effects of histamine and reactions of hyper-sensitivity. These are intended to treat the symptoms of a certain number of allergic signs, in particular of the skin and mucous membrane. They are prescribed for the main indications of allergic rhinitis, allergic dermatosis (papulo-oedematous forms), Quincke oedema, against the side effects of desensitisation treatment, to treat serum sickness and allergic reactions to medicines.

These anti-H1s are grouped under a classification derived from their chemical structure. A distinction is made between five main classes:
  ethylene diamines
  benzhydryl alkylamines
  benzhydryl piperazines
  pridylbenzyl alkylamines, and
  phenothiazinyl alkylamines.

Among these families, the phenothiazinyl alkylamines are powerful H1 antihistamines but they sometimes exhibit properties against receptors of other biogenic amines.

The present invention therefore concerns the use of at least one antihistaminic agent, or the use of at least one antihistaminic agent or its addition salts to a pharmaceutically acceptable acid or base, for the preparation of a medicinal product intended to be used for the preventive or early treatment of arthritis of viral origin, and in particular arthritis of the distal joints.

One advantageous aspect of the invention concerns the use of at least one antihistaminic agent to prepare a medicinal product intended for the preventive or early treatment of inflammatory syndromes of viral origin, triggered by an alphavirus, in particular the Chikungunya virus, River Ross virus and Barmah Forest virus.

Chikungunya is an infectious tropical disease due to an arbovirus of the Togaviridae family (alphavirus) transmitted by mosquitoes of genus *Aedes*. *Aedes* reproduce easily in stagnant freshwater, and in the shade. The larval sites are abandoned receptacles, for example swimming pool tarpaulins, abandoned tyres . . . .

These species are also involved in the transmission of other arboviruses, such as the Dengue and yellow fever viruses etc. . . .

Contamination of healthy individuals is caused by the saliva of infected female mosquitoes. The transmission of the virus from an affected person to a mosquito is made via the blood sucked on biting, the blood then passes through the mosquito's stomach barrier to enter into the salivary glands. The incubation time of the disease is 4 to 7 days.

Signs of onset of the disease are high fever followed by erythema and very painful joint stiffness chiefly affecting the small joints of the wrists, ankles and feet. The pain is of inflammatory type, very strong in the morning and being somewhat relieved by gentle movements. Swelling of the joints may occur.

This strong joint pain is associated with stiffness (bent appearance of patients). Skin signs consist of papular or maculopapular rashes reaching the torso and limbs, accompanied by pruritus and irritation. In the severest cases, these symptoms may be accompanied by headache, nausea and vomiting. However, asymptomatic forms of the disease also exist.

At the current time no medicinal product has been developed and no vaccination has been finalized. Also no viricidal treatment exists. Treatment is therefore solely symptomatic and consists of reducing temperature and pain.

Amongst the antihistamines suitable for implementing the present invention, preference is given to H1 antihistamines and in particular those chosen from among acrivastin, astemizole, azelastin, betotastine, brompheniramine, buclizine, carbinoxamine, carpiramine, cetirizine, chlorphenamine, clemastin, cyproheptadine, desloratadine, dexchlorpheniramine, diphenhydramine, doxepine, ebastin, emedastin, epinastin, eprozinol, fenspiride, fexofenadine, homochlorcyclidine, ketotifen, hydroxyzine, isothipendyl, levocarbastin, levocetizirine, loratadine, mepyramine, mizolastin, olopatadin, oxatomide, oxetorone, pimethixene, pizotifen, rupatidine, sebastin, terfenadin, tripelenamine, tripolidin, and the compounds of the phenothiazine family.

Particularly advantageously, amongst the phenothiazines, those chosen are alimemazine, aminopromazine, chlorpromazine, cyamemazine, isopromethazine, levopromazine, mequitazine, pipotiazine, promethazine, thioridazine and thiazinamium methylsulfate. One phenothiazine that is particularly suited for the novel use according the present invention is mequitazine.

The above active ingredients and those indicated below are called by their International Non-Proprietary Name (INN).

The Applicant has also evidenced that the treatment of joint inflammation according to the present invention can be considerably improved if the compounds used, in addition to their antihistaminic activity, contain an antiserotonin component. Serotonin is another vasoactive amine involved in the inflammatory process, and has an influence on vascular permeability.

According to this other aspect, the invention therefore concerns the use of at least one antihistaminic agent to prepare a medicinal product intended for the preventive or early treatment of inflammatory syndromes of viral origin, such as defined above and more particularly those triggered by an alphavirus, characterized in that said antihistaminic agent also contains an antiserotonin component. Preferably an H1-antihistamine is chosen having an antiserotonin component, and advantageously a compound chosen from among aminopromazine, azatadine, carpripramine, chlorpromazine, clemastine, cyproheptadine, eprozinol, fenspiride, isothipendyl, oxatomide, oxetorone, pimethixene, pizotifen, and compounds of the phenothiazine family, in particular alimemazine, chloropromazine, cyamemazine, levopromazine, mequitazine, pipotiazine, thioridazine.

To implement the present invention, the compounds may have one or more asymmetric centres in their chemical structure. In this case, the use according to the invention concerns both compounds in the form of a racemic mixture and those in the form of only one of the possible epimers, diastereoisomers or enantiomers.

The invention also concerns the use of compounds according to the present invention in the form of their additions salts with a pharmaceutically acceptable acid or base.

Among the pharmaceutically acceptable acids, non-limiting mention may be made of hydrochloric, hydrobromic, sulphuric, phosphonic, acetic, trifluoroacetic, lactic, pyruvic, malonic, succinic, glutaric, fumaric, tartaric, maleic, citric, ascorbic, methansulfonic, camphoric, axalic acids . . . .

Among pharmaceutically acceptable bases, non-limiting mention may be made of sodium hydroxide, potassium hydroxide, triethylamine, tertbutylamine, . . . .

The present invention concerns the use such as defined above, characterized in that the medicinal product is in the form of a pharmaceutical composition adapted for any usual form of administering. These pharmaceutical compositions contain at least one antihistaminic compound such as defined previously, used within the scope of the present invention, either alone or in combination with one or more pharmaceutically acceptable excipients.

Among these pharmaceutical forms, particular mention may be made of those suitable for oral, parenteral, per- or transcutaneous, rectal, lingual or sublingual administering, and in particular plain or coated tablets, sublingual tablets, sachets, packs, capsules, bars, suppositories, creams, ointments, drinkable vials, vials for injection and/or solutes, syrups. Dosage varies with the patient's age and weight, the chosen route of administration and possible associated treatments.

According to one preferred aspect of the invention, the medicinal product is in the form of a tablet whose dose of antihistaminic agent such as defined previously lies between 0.5 mg and 200 mg, and more particularly between 5 mg and 100 mg. Preferably this antihistaminic agent is mequitazine.

According to another advantageous aspect of the invention, the medicinal product is in the form of a syrup whose concentration of antihistaminic such as defined previously ranges from 0.01% to 1%, i.e. varies between 0.1 mg/ml and 10 mg/ml. Preferably this antihistaminic agent is mequitazine.

The medicinal product may also be in the form of capsules whose dosage of antihistaminic agent such as defined previously varies between 0.1 mg and 15 mg, in the form of drinkable solutions whose concentration of antihistaminic agent such as defined previously varies between 1 mg/ml and 70 mg/ml, or in the form of a solute for injection in particular in 2 ml vials whose concentration of antihistaminic agent such as defined previously varies between 5 mg/ml and 50 mg/ml.

According to another aspect, the present invention concerns a combination product of at least one antihistaminic agent and at least one antiserotonin agent for its simultaneous, separate or time-release use in preventive or early treatment of inflammatory syndromes of viral origin, and more particularly those triggered by an alphavirus, and more specifically the Chikungunya virus.

The choice of the antiserotonin agent or agents to be associated with the antihistaminic agent or agents in the product of the invention, is made in relation to the extent of the antagonist nature of the antihistaminic compound. For example, the simultaneous action on both the histaminic and serotoninergic receptors may be modulated by the association of two suitable agents.

Advantageously, in the product of the invention, the antihistamine is an H1-antihistamine, e.g. chosen from among acrivastin, astemizole, azelastin, betotastine, brompheniramine, buclizine, carbinoxamine, carpipramine, cetirizine, chlorphenamine, clemastin, cyproheptadine, desloratadine, dexchlorpheniramine, diphenhydramine, doxepine, ebastin, emedastin, epinastin, fenspiride, fexofenadin, homochlorcyclidine, ketotifen, hydroxyzine, levocarbastine, levocetizirine, loratadine, mepyramine, mizoelastin, olopatadin, oxatomide, oxetorone, pimethixene, pizotifen, rupatidine, sebastin, terfenadin, tripelenamine, tripolidine and compounds of the phenothiazine family. Preferably, among the compounds of the phenothiazine family those chosen are alimemazine, chlorpromazine, cyamemazine, isopromethazine, levopromazine, mequitazine, pipotiazine, promethazine, thioridazine and thiazinamium methylsulfate. One particularly suitable phenothiazine is mequitazone.

Among the antiserotonin compounds suitable for implementing the present invention, mention may be made of the antagonists of the $5-HT_{2A}$, $5-HT_{2C}$ and/or $5-HT_3$ receptors. Those chosen are for example amixetrine, bencyclane, chlorphenoxamine, chlorprothixene, dimetotiazine, fenpentadiol, medifoxamine, methdilazine, perizacine, oxaflumazine, risperidone, ritanserin, seroquel, olanzapine, mesulergin, mianserin, ritanserin, granisetron, dihydroergotamine, dolasetron, ondensteron, ergotamine, flopropione, ketanserin, methylergometrine, methysergide, naftidrofuryl, tolazoline and tropisetron.

The present invention is illustrated by the following examples which are in no way limiting thereof. The use of antihistaminic agents according to the invention can be shown by observational studies and clinical trials conducted following standard techniques and methodologies.

EXAMPLE 1

Tablet Containing 5 or 10 mg Mequitazine

| | |
|---|---|
| Mequitazine (INN) | 5 mg (or 10 mg) |
| Monohydrated lactose | q.s. |

-continued

| | |
|---|---|
| Corn starch | q.s. |
| Gum arabica | q.s. |
| Anhydrous colloidal silica | q.s. |
| Talc | q.s. |
| Sodium carboxymethyl starch | q.s. |
| Magnesium stearate | q.s. |

EXAMPLE 2

Syrup Containing Mequitazine

| | |
|---|---|
| Mequitazine (INN) | 1.25 mg/per ms.sp.* |
| Ascorbic acid | q.s. |
| Soluble essence of Mandarin | q.s. |
| Sucrose | q.s. |
| Purified water | q.s. |
| Preservatives | q.s.** |

(*per ms.sp. = per 2.5 ml measuring spoon)
(**quantum sufficit)

EXAMPLE 3

Effect of Mequitazine on the Preventive and Early Treatment of Inflammatory Syndromes Caused by the Chikungunya Virus—Results of an Observational Study Protocol:

104 patients were included in this observational study involving a limited number of doctors held secret: mean age 39.6 years, 61.9% female.

At the time of inclusion at D0, the patients were slightly feverish with a mean temperature of 38.4° C.

The patients consulted after various periods following the onset of hyperthermia, but generally 1.1 days after this onset, the phase preceding the onset of arthralgia.

During this first visit, the most painful joints were the fingers, wrists and ankles.

At this first visit on D0, the doctors gave mequitazine to the patients, possibly in combination with an anti-inflammatory.

A questionnaire was handed to each patient and completed with the patient.

This questionnaire included the content of 2 conventional questionnaires:

HAQ* questionnaire (Health Assessment Questionnaire) to assess the functional capacity of patients (function index) i.e. the handicap generated by the pathology;

A SF12** questionnaire to assess the quality of life of the patient using the SF12 score.

At D7 and D14 the patient again filled in these questionnaires.

At D28, at the time of a further consultation, these questionnaires were again updated.

HAQ: Bruce B and Fries J. The Stanford Health Assessment Questionnaire (HAQ): A review of its history, issues, progress and documentation. J. Rheumatol. 2003; 30(1):167-78.

SF12: Ware J Jr, Kosinski M, Keller S D. A 12-item Short-Form Health Survey: construction of scales and preliminary tests of reliability and validity. Med. Care 1996; 34:220-33.

Results:

Statistical analysis of these questionnaires gave the following results:
- Measurement of handicap generated by the pathology (HAQ function index): the administering of mequitazine leads to a statistically significant improvement at D14 and D28.
- Between D0 and D7, mequitazine leads to a significant decrease in the number of painful joints, this decrease continuing in time.
- The earlier a patient consults, and hence the earlier mequitazine is prescribed, the more physical recovery is swift and extensive (SF12 scale and HAQ test).
- The combining of an anti-inflammatory with mequitazine does not have an influence on the SF12 physical score measuring quality of life.

The invention claimed is:

1. A method of early treatment of arthritis of viral origin which comprises, administering to a patient in need thereof an effective amount of a medicinal product comprising at least one antihistaminic agent, or its addition salts to a pharmaceutically acceptable acid or base.

2. Method according to claim 1, wherein the arthritis of viral origin is triggered by an alphavirus.

3. Method according to either of claims 1 and 2, wherein said medicinal product also contains an antiserotonin component.

4. Method according to claim 1, wherein the antihistaminic agent is an H1-antihistamine.

5. Method according to claim 4, wherein the antihistaminic agent is selected from the group consisting of alimemazine, aminopromazine, chlorpromazine, cyamemazine, isopromethazine, levopromazine, meqitazine, pipotiazine, promethazine, thioridazine and thiazinamium methylsulfate.

6. Method according to claim 1, wherein said medicinal product is in the form of a tablet whose dose of antihistaminic agent ranges from 0.5 mg to 200 mg.

7. Method according to claim 6, wherein the antihistaminic agent is mequitazine.

8. Method according to claim 1, wherein said medicinal product is in the form of a syrup whose concentration of antihistaminic agent lies between 0.01 and 1 weight-volume percentage.

9. Method according to claim 8, wherein the antihistaminic agent is mequitazine.

10. The method according to claim 1, wherein the arthritis is arthritis of the distal joints.

11. The method according to claim 2, wherein the alphavirus is Chikungunya virus, Ross River virus or Barmah Forest virus.

12. The method according to claim 4, wherein the H1-antihistamine is a phenothiazine compound.

* * * * *